(12) United States Patent
Juhnke et al.

(10) Patent No.: US 10,918,571 B2
(45) Date of Patent: Feb. 16, 2021

(54) CONTAINER FOR A LIQUID MEDICAMENT

(71) Applicant: Sanofi-Aventis Deutschland GMBH, Frankfurt am Main (DE)

(72) Inventors: Hanno Juhnke, Frankfurt am Main (DE); Jan-Peter Spengler, Frankfurt am Main (DE); Michael Schrack, Pliezhausen (DE)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 131 days.

(21) Appl. No.: 16/095,007

(22) PCT Filed: Apr. 20, 2017

(86) PCT No.: PCT/EP2017/059321
§ 371 (c)(1),
(2) Date: Oct. 19, 2018

(87) PCT Pub. No.: WO2017/182540
PCT Pub. Date: Oct. 26, 2017

(65) Prior Publication Data
US 2019/0151198 A1 May 23, 2019

(30) Foreign Application Priority Data
Apr. 21, 2016 (EP) .................................. 16166383

(51) Int. Cl.
*A61J 1/10* (2006.01)
*A61J 1/06* (2006.01)
(Continued)

(52) U.S. Cl.
CPC .................. *A61J 1/067* (2013.01); *A61J 1/10* (2013.01); *A61M 5/148* (2013.01); *A61M 5/152* (2013.01); *A61M 5/2425* (2013.01); *A61M 39/24* (2013.01)

(58) Field of Classification Search
CPC ............ A61J 1/067; A61J 1/10; A61M 5/148; A61M 39/24; A61M 5/152; A61M 5/2425
See application file for complete search history.

(56) References Cited

U.S. PATENT DOCUMENTS 2,764,979 A 10/1956 Edward
4,318,400 A 3/1982 Peery et al.
(Continued)

FOREIGN PATENT DOCUMENTS

AU 414085 6/1971
CN 102151346 8/2011
(Continued)

OTHER PUBLICATIONS

International Preliminary Report on Patentability in Application No. PCT/EP2017/059321, dated Oct. 23, 2018, 9 pages.
(Continued)

*Primary Examiner* — Amber R Stiles
(74) *Attorney, Agent, or Firm* — Fish & Richardson P.C.

(57) ABSTRACT

The present disclosure relates to a container for a liquid medicament, comprising at least one flexible casing forming at least one cavity configured to receive the medicament, wherein the casing comprises a first wall portion and a second wall portion, wherein the second wall portion is located opposite to the first wall portion, at least a first outlet in fluid connection with the cavity and extending through the casing and multiple filaments extending through the cavity wherein each of the multiple filaments comprises a first end and a second end, wherein the second end is opposite to the first end, and wherein each of the first ends of the filaments are connected to the first wall portion and each of the second ends of the filaments are connected to the second wall portion.

18 Claims, 5 Drawing Sheets

(51) Int. Cl.
  *A61M 5/24*  (2006.01)
  *A61M 5/148*  (2006.01)
  *A61M 5/152*  (2006.01)
  *A61M 39/24*  (2006.01)

(56) References Cited

U.S. PATENT DOCUMENTS

| | | |
|---|---|---|
| 4,360,736 A | 11/1982 | Weissenfluh |
| 4,795,432 A | 1/1989 | Karczmer |
| 2007/0297701 A1* | 12/2007 | Engel ............... B65D 33/02 393/104 |

FOREIGN PATENT DOCUMENTS

| | | |
|---|---|---|
| CN | 104487112 | 4/2015 |
| CN | 204723399 | 10/2015 |
| CN | 105683060 | 6/2016 |
| EP | 0960628 | 12/1999 |
| JP | H07206007 | 8/1995 |

OTHER PUBLICATIONS

International Search Report and Written Opinion in International Application No. PCT/EP2017/059321, dated Jul. 17, 2017, 12 pages.

\* cited by examiner

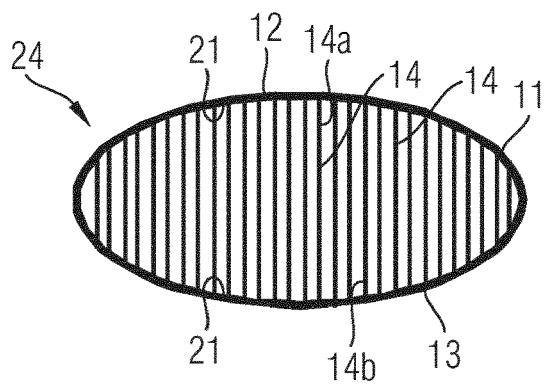
Fig. 15 A-A
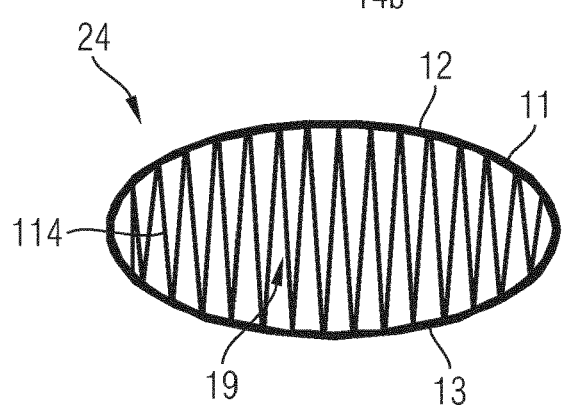
Fig. 16 A-A
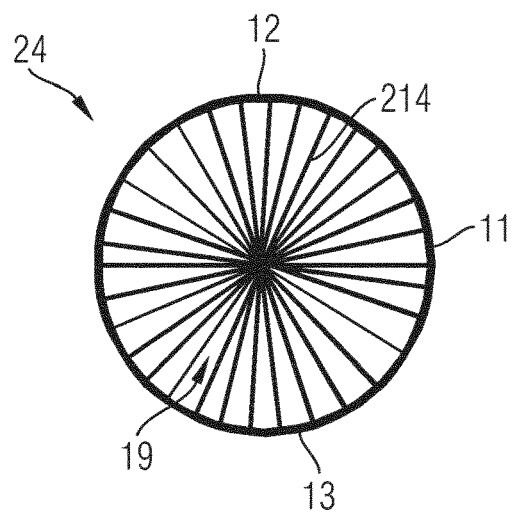
Fig. 17 A-A
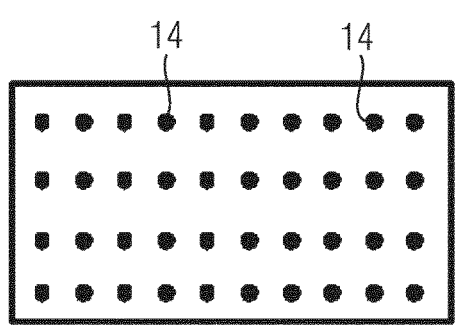
Fig. 18 B-B
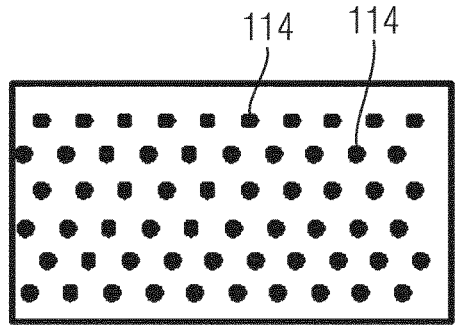
Fig. 19 B-B

CONTAINER FOR A LIQUID MEDICAMENT

CROSS REFERENCE TO RELATED APPLICATIONS

This application is a U.S. national stage application under 35 USC § 371 of International Application No. PCT/EP2017/059321, filed on Apr. 20, 2017, which claims priority to European Application No. 16166383.6, filed on Apr. 21, 2016, the entire contents of which are incorporated herein by reference.

DESCRIPTION

The present disclosure relates to a container for a liquid medicament and in particular to a flexible container for a liquid medicament. In another aspect, the disclosure relates to a drug delivery device to cooperate with such a container for administering a dose of the medicament, e.g. by way of injection.

BACKGROUND

Drug delivery devices for setting and dispensing a single or multiple doses of a liquid medicament are as such well known in the art. Generally, such devices have substantially a similar purpose as that of an ordinary syringe. Drug delivery devices, in particular injection devices, have to meet a number of user-specific requirements. For instance with patients suffering chronic diseases, such as diabetes, the patient may be physically infirm and may also have impaired vision. Drug delivery devices may be particularly intended for home medication. They need to be robust in construction and should be easy to use. Manipulation, configuration and the general handling of the device and its components should be intelligible and easily understandable. Setting of a dose and a subsequent dispensing of a dose of a medicament should be easy to operate and unambiguous.

The medicament to be dispensed by a drug delivery device is typically provided in a multi-dose cartridge. Conventional cartridges typically comprise a vitreous barrel sealed in distal direction by means of a pierceable seal and being further sealed in proximal direction by a piston slidably arranged therein. The piston is displaceable towards the distally located seal by means of a drive mechanism of the drug delivery device. The drive mechanism, typically comprising a piston rod or a plunger displaceable in a longitudinal axial direction is configured to exert a distally directed thrust onto the piston of the cartridge that is positionally fixed inside the drug delivery device. By displacing the piston of the cartridge for a well-defined axial distance a well-defined amount of the liquid medicament located inside the cartridge will be expelled through the seal of the cartridge and due to the displacement of its piston towards the distally located seal. Typically, the distally located seal of the cartridge is pierced by a piercing element, such as a double-tipped injection needle.

Vitreous barrels of conventional cartridges for liquid medicaments are comparatively prone to breaking or fracture. Filling of such cartridges and their general handling in a mass manufacturing process or mass assembly process is therefore rather delicate. Expenses and expenditures for handling of vitreous cartridges are comparatively high, which comes along with comparatively large costs for cartridge production, cartridge assembly as well as cartridge logistics.

There exist also flexible bags and medicament containers. But use of flexible bags is mainly restricted to suction-based withdrawal of the liquid medicament from the interior of a flexible bag. Flexible medicament containers are therefore mainly limited to suction pump-based delivery mechanisms of drug delivery devices, such as infusion pumps.

Use of a flexible bag in a drug delivery device, wherein the medicament is expelled from the bag through a compression of the bag is rather difficult to control. A comparatively high degree of flexibility which is inherent to flexible bags has a rather negative impact on dosing accuracy. This makes it almost impossible to provide sufficiently precise dose dispensing and dose administering. To improve dosing accuracy with flexible bags it has been suggested to arrange the flexible bag in a dimensionally stable housing. However, such an additional housing increases the number of parts of the medicament container and/or the number of parts of a corresponding drug delivery device. In addition the generic flexibility of a flexible bag is then no longer useable.

Some aspects of the disclosure can be implemented to provide a container for a liquid medicament, which is generally flexible and which supports a pressure-based dispensing of the medicament located therein thereby providing a high degree of dosing accuracy without the necessity to house the flexible container inside a geometrically or dimensionally stable mechanical structure. Some aspects of the disclosure can be implemented to provide a container for a liquid medicament that is rather flexible in terms of its outer shape and geometry. Moreover, the flexible container should be easily adaptable to different drive mechanisms of drug delivery devices. It should be easily configurable as a single cavity- or single chamber container as well as a multiple cavity- or multiple chamber container. In addition, the flexible container should be producible at low or moderate costs in large quantities. The container should be capable for both, dispensing of a liquid substance as well as receiving of a fluid in exchange of the liquid substance, e.g. the liquid medicament.

SUMMARY

In a first aspect a container for a liquid medicament is provided. The container comprises at least one flexible casing forming at least one cavity to receive the medicament. The container further comprises at least a first outlet in fluid connection with the cavity and extending through the flexible casing. The casing comprises a first wall portion and a second wall portion. The second wall portion is basically located opposite to the first wall portion. Typically, an inside facing side of the first wall portion faces towards an inside facing side of the second wall portion and vice versa. There are further provided multiple filaments each of which extending through the cavity and each of which having a first end and a second end. First and second ends of the filaments define opposite ends thereof. The filaments are configured or designed as longitudinally extending strands or strings. The first end of each filament is connected to the first wall portion and the opposite end, hence the second end of each filament, is connected to the second wall portion. In this way the multiple filaments form multiple connectors between first and second oppositely located wall portions of the casing and the filaments extend through the cavity.

By means of the multiple filaments the flexible casing can be stabilized. Especially when subject to an inside pressure, the flexible casing is expandable so that the multiple filaments are tensed or strained. By having multiple filaments punctually and locally interconnecting first and second wall portions of the flexible casing, the overall geometric shape of the flexible casing can be stabilized and therefore becomes geometrically stable even when subject to an external pressure acting on the flexible casing from outside.

The filament-based stabilization of the flexible casing enables that the flexible casing may be subject to a well-defined local deformation so as to reduce the volume of the cavity without modifying the overall geometric shape of the flexible casing. In this way, the container and the flexible casing are particularly suitable for a pressure-based withdrawal of the liquid medicament from the cavity of the container. The flexible casing may be locally deformable in a way defined by the geometry and the configuration of the various filaments. In this way, the container enables a rather high degree of dosing accuracy for a pressure-based dispensing of the liquid medicament from the cavity.

The casing with the first and second wall portions and the filaments connected there between form a kind of a so-called 'dropstitch fabric'. Two oppositely located inwardly facing wall portions of the casing are mutually connected by numerous tension-stable filaments. When subject to an elevated hydrostatic pressure or fluid pressure inside the casing, the casing remains dimensionally stable. It is then also rather tear-resistant.

According to a further embodiment the filaments are tension-stable. The filaments are substantially non-extendable or non-stretchable. Each one of the filaments may be flexible and may be deformable as long as the first and the second wall portions are separated by a minimum or medium distance. Separating the first and the second wall portion to a maximum degree of separation immediately leads to a tensioning and straining of the filaments. Since the filaments are substantially non-stretchable and since the filaments are hence tension-stable the filaments effectively prevent a separation of first and second wall sections to a degree larger than an allowable maximum distance.

The maximum distance between oppositely located first and second wall portions of the flexible casing is defined and limited by the length of the respective filaments extending between first and second wall portions. Since the filaments are tension-stable and hence non-stretchable said filaments provide structural and geometric stability to the flexible casing as soon as the cavity formed by the flexible casing is pressurized.

According to another embodiment the cavity is inflatable to a maximum volume and to a predefined inside pressure at least until the filaments are tensed and straight-lined. When inflated to the maximum volume the first and second wall portions are separated by their maximum allowable distance. Inflating of the cavity includes filling of the cavity with a fluid, i.e. with a liquid fluid or with a gaseous fluid or mixtures thereof. By filling the cavity with a fluid the cavity is inflatable to a maximum volume and to a predefined inside pressure inside the cavity.

Pressurizing the cavity to a predefined inside pressure leads to a separation of oppositely located first and second wall portions. Consequently, the filaments extending between first and second wall portions become subject to tension and strain. Consequently, the filaments, which may be flexible, will become straight-lined or straight-shaped. As soon as the cavity is inflated to the predefined pressure level at least some or all of the filaments are tensed or strained. A bending or a local deformation of the inflated flexible casing is effectively prevented by the tensed or strained filaments.

Bending or deforming of the inflated flexible casing would come along with a further stretching or bending of at least one or several of the filaments. Since the filaments are tension-stable, such a further stretching of selected filaments is not possible and is effectively impeded by the non-stretchable properties or characteristics of the filaments. In this way and while the filaments are straight-lined or stretched to their maximum extension they effectively prevent any local deformation of the inflated flexible casing.

According to another embodiment the casing itself, its first and second wall portions and the cavity formed by the casing are non-expandable or non-stretchable beyond the maximum volume. Typically, the casing and the material the casing is made of is flexible but non-stretchable. Making use of a non-stretchable casing and non-stretchable first and second wall portions, the mechanical and structural stability of the container can be enhanced once it is inflated to the maximum volume.

By means of the multiple filaments the container and the flexible casing can be manufactured and provided in almost any geometric shape. Due to the filaments selected wall portions of the flexible casing can be kept at a maximum distance, which is eventually shorter than a distance the respective wall portions would be separated if such filaments there between would be absent.

In effect, the flexible casing may be of cylindrical shape. It may be of a bulged or bulb shape. The flexible casing may comprise a toroidal shape or any other arbitrary geometric shape defined by the specific configuration, arrangement and geometric extension of the various filaments.

In another embodiment the outlet of the container extends through the flexible casing. An inside facing portion of the outlet is hence in fluid communication with the cavity. It may even contribute to a confinement or boundary of the cavity. An outside portion of the outlet is located outside the cavity and may constitute or form a part of the outer appearance of the container.

According to another embodiment the first outlet comprises at least one of a pressure regulator and a throttle valve. By means of a pressure regulator or a throttle valve the cavity can be kept at an inside pressure that is larger than the environmental pressure. By means of the pressure regulator or by means of a respective throttle valve the inside pressure of the container can be kept above a minimum threshold that is required to keep at least some of the filaments tensed, strained and/or straight-lined. By means of the pressure regulator or throttle valve implemented in the outlet a well-defined pressure-based dispensing of the medicament from the cavity can be provided.

It is hence conceivable, that the pressure regulator or the throttle valve are pressure regulated so that only a well-defined amount of the medicament is dispensable through the pressure regulator and the throttle valve as long as the inside pressure of the flexible casing is above an initial pressure value. Raising of the inside pressure above an initial pressure may be conducted by exerting a pressure to the casing from outside, e.g. by squeezing or compressing the casing in a well-defined way. By exerting an external pressure to the flexible casing, the inside pressure may be raised above an initial pressure value. Consequently, the pressure regulator or the throttle valve may open and may allow dispensing of a well-defined amount of the medicament there through until the inside pressure drops to the initial pressure value at which the pressure regulator and/or the throttle valve effectively seals the cavity of the container.

By means of a pressure regulator or a throttle valve implemented into the outlet of the container a required inside pressure of the cavity can be maintained thus leading to the structural stability of the flexible casing. At the same time the pressure regulator or the throttle valve may provide a well-defined pressure-based or pressure-controlled dispensing of the liquid medicament from the cavity.

According to another embodiment the casing is of elongated shape and extends in an axial direction (z). The casing comprises a distal end section and a proximal end section separated along the axial direction. In other words the distal and the proximal directions extend along the axial direction. The casing of elongated shape may therefore extend substantially in axial direction. It may comprise a tubular shape either with a circular symmetric cross-section or with an oval cross-section. The casing may comprise or form a cylindrical sidewall and may comprise a bottom wall extending substantially perpendicular to the cylindrically-shaped sidewall. In other embodiments the casing may be a single pieced and may be seamless or it may be formed e.g. by welding of two substantially equally-shaped layers along a seam, e.g. extending in axial direction. In such embodiments the casing may be somewhat bottomless and may converge, e.g. towards the proximal end section. Hence, the proximal end section may be convex-shaped and may further comprise a constantly reducing cross-section towards its free end. When the casing and hence the entire container is of elongated shape it may be usable with existing drug delivery devices and existing drive mechanisms. Generally, a casing of elongated or tubular shape may be configured to replace or to substitute conventional cartridges with a vitreous barrel.

In another embodiment the first outlet is located at the distal end section and the proximal end section of the casing is deformable or squeezable towards the distal end section. In particular, the proximal end section may be compressible towards the distal end section so that the entire container is compressible in axial direction. Typically, the container is compressible along a direction substantially perpendicular to the extension of the various filaments. Typically, the container is compressible by exerting a pressure to the proximal end section thereof that is larger than the predefined inside pressure inside the cavity. Application of such a comparatively large pressure to the proximal end section of the container leads to an increase of the inside pressure in the interior of the cavity. Due to the pressure regulator or the throttle valve of the outlet such an increased pressure may be relieved by expelling a well-defined amount of the liquid medicament through the outlet.

Since the casing itself is generally flexible it is easily deformable, squeezable or compressible towards the distal end section, thereby urging a well-defined amount of the medicament out of the cavity.

The squeezing or compression of the flexible casing enables a complete emptying of the cavity and a complete removal of the medicament from the cavity. There is no longer a need for a separate piston sliding along an inside facing sidewall portion of a tubular-shaped cartridge. So there is no longer a need for a displaceable or moveable component inside the container. Since the flexible casing may be made of an elastic material it provides a rather high degree of flexibility. It is also less prone to breakage or fracture and is hence rather break- and fracture-resistant. In addition to that a flexible casing, e.g. made of a suitable plastic material is rather inexpensive to manufacture especially in large quantities. It may be fillable in a sterile environment and may provide a rather high degree of closure integrity. Depending on the specific choice of a material for the flexible casing the cavity is hence impervious to liquid substances and/or impervious to gaseous substances.

According to another embodiment the proximal end section of the casing is coilable towards the distal end section. Hence, the container may be configured and shaped like a collapsible tube. It may converge towards the proximal end section. Near or at the proximal end section first and second wall portions may be located at a comparatively small distance so that first and second wall portions may be squeezed and pressed directly onto each other. Thereafter, the collapsed first and second wall portions may be subject to a coiling motion thereby successively inducing a collapsing of first and second oppositely located neighboring first and second wall portions onto each other. By means of a coiling motion a well-defined collapsing, compression and squeezing of the cavity and of the flexible casing can be obtained, thus allowing to improve dosing accuracy of a respective drug delivery device.

In another embodiment at least some of the filaments are located in and extend along an imaginary plane or virtual plane extending substantially perpendicular to the axial direction of the casing. In this way, the filaments especially provide structural stability in the imaginary plane as long as the inside pressure is kept at the predefined initial pressure value. In a direction perpendicular to the imaginary plane, hence along the axial direction the structural stability of the container and hence of its flexible casing may be exclusively provided by the inside pressure. In this way the flexible casing is deformable, squeezable or compressible along the axial direction and hence in a direction perpendicular to the extension of the various filaments. In this way a selected or predefined axial portion of the flexible casing is collapsible in axial direction while a residual axial portion of the casing and hence of the cavity remains structurally stable and geometrically unaltered. It is conceivable that there exist several of such imaginary planes that are mutually separated by the distance between axially adjacently located filaments. The filaments may be arranged in a regular or irregular two-dimensional pattern perpendicular to the elongation of the various filaments.

In another embodiment at least some of the filaments extend substantially parallel to each other. The filaments may be arranged according to a regular pattern. They may be arranged according to a square or rectangular pattern, i.e. the various filaments are located at the corners of regular quadratic or rectangular structures. Alternatively, the filaments may be arranged according to a hexagonal pattern. The filaments may be thus located at the corners of regularly-shaped triangles or hexagons. The density of filaments is comparatively high. Across the entire cavity there may be at least 10 filaments, 50 filaments, 100 filaments or even more than 200 filaments. Typically, the filaments are homogeneously distributed across the cavity. Alternatively, there may be provided an inhomogeneous spatial distribution of filaments. Hence, there may be portions of the cavity having a higher density of filaments than other portions of the cavity. By means of an inhomogeneous filament distribution throughout the cavity the collapsing behavior of the cavity in response to application of an external pressure can be controlled or defined.

In other embodiments at least some of neighboring filaments form a zigzag structure between first and second wall portions of the cavity. Here, neighboring filaments extend at predefined and alternating angles with respect to the first or second wall portion.

Typically, the first ends of two neighboring filaments are connected to the first wall portion at a common connecting point. Likewise, the second ends of two neighboring filaments are connected to the second wall portion at a common connecting point. When considering a first and a second filament connected with their first ends to a common connecting point of the first wall portion their second ends will be located at a predefined distance from each other. This predefined distance is given by the length of the filaments and by an angle at which the first filament extends relative to the second filament. The second ends of the first and the second filaments are connected with second ends of a third and a fourth filament, respectively.

In another embodiment at least some of the filaments extend in a radial direction with regards to the axial direction (z). Here, the axial direction coincides with a symmetry axis of the container. It is also conceivable, that the filaments extend in accordance to a helical structure so that filaments neighboring in an axial direction are rotated by a predefined angle with the axial direction as an axis of rotation. With a circular symmetric outer shape of the cavity at least with regards to the axial direction as a symmetry axis it is of particular benefit when the radially extending filaments all extend through the longitudinally extending symmetry axis. With an oval-shaped cross-section of the cavity the filaments always extend from the first wall portion to the diametrically oppositely located second wall portion and vice versa.

The choice of one of the above described filament configurations depends on the specific application scenario and the dispensing mechanism of a drug delivery device for which the container is configured.

In another embodiment the container comprises a separation wall dividing the cavity into a first sub-cavity and into a second sub-cavity. The container further comprises a second outlet. Here, the second outlet is in fluid connection with the second sub-cavity whereas the first outlet is in fluid connection with the first sub-cavity. Both sub-cavities may constitute the interior of the flexible casing. Both sub-cavities may each comprise multiple filaments like the at least one cavity as described above. So each one of the first and second sub-cavities comprises a first wall portion and a second wall portion, wherein multiple filaments extend between first and second wall portions of each one of the first and second sub-cavities. In this way, each sub-cavity can be separately structurally stabilized by means of the multiplicity of filaments and when inflated to a maximum volume.

By having a first and a second sub-cavity the container is configured to receive at least two different medicaments. In this way the container is a multi-chamber container, wherein each sub-cavity forms a chamber for a separate liquid medicament.

First and second sub-cavities are configurable for a simultaneous dispense of at least two different liquid medicaments. Depending on the specific geometry and configuration of first and second sub-cavities it is also conceivable, that different medicaments are dispensable sequentially and according to a predefined temporal dispensing schedule. By making use of different sub-cavities, that may be of different volume and by providing a simultaneous deformation, squeezing or compression of the entire flexible casing a constant or variable mixing ratio of the at least two different liquid medicaments expelled from the first sub-cavity via the first outlet and expelled from the second sub-cavity via the second outlet can be obtained. So the mixing ratio may be simply defined and governed by the geometric shape of the first and second sub-cavities. A mixing ratio for a simultaneous dispensing of at least two different liquid substances is for instance governed by different cross sections of first and second sub-cavities in a plane perpendicular to a dispensing or squeezing direction along which the flexible casing is to be squeezed for expelling the liquid substance.

In principle the container is not limited to only two sub-cavities. By making use of not only one but several separation walls the total number of sub-cavities can be increased to three or even more sub-cavities.

It is even conceivable that two individual containers are mutually connected along at least one of their sidewalls. Then, the mutually interconnected sidewalls of a first casing and a second casing behave and act like a separation wall inside a single common flexible casing.

In another embodiment the first outlet and a second outlet are located at opposite end sections of the casing, wherein the casing is elongated along an axial direction. The casing may have a tubular or oval cross section. It may be formed from a tube or it may comprise a tube or hose. Furthermore, the casing is configured to become compressed by a squeezing member in a direction perpendicular to the axial direction to form a first sub-cavity and a second sub-cavity. The sidewalls or a single sidewall, e.g. tubular shaped side wall, of the casing are compressible or is compressible in a transverse or lateral direction, i.e. perpendicular to the longitudinal elongation of the casing to such an extent that side wall sections of the casing located oppositely in transverse or lateral direction get in mutual contact, typically in a fluid-tight way.

The squeezing member is configured to interact with an outside section of the sidewall along the entire transverse extension of the sidewall. In this way, and by squeezing oppositely located sidewall sections of the casing, a first and a second sub-cavity will be formed, that are separated by the laterally compressed sidewall sections. The first and the second sub-cavities are located adjacent to each other in axial direction. They are separated in axial direction by the inwardly squeezed sidewall section(s). The compressed and hence collapsed sidewall section(s) may form a kind of a separation wall between the first and the second sub-cavities. In this way and only by means of a local and inwardly directed deformation of the sidewall(s) of the flexible casing a kind of a hermetic separation between first and second sub-cavities can be provided. Since the separation wall is exclusively formed by a local deformation of at least one of the first and the second sidewall portions the position of the separation wall is dynamically modifiable.

In addition to that the squeezing member is configured to be displaced along the axial direction to increase the size of the second sub-cavity at the expense of the size of the first sub-cavity or vice versa. Typically, the squeezing member is displaceable along the axial direction while being compressed laterally or transversally against the outside of the sidewall. The axial displacement can be induced by a drive member, such like an electro-mechanical or pneumatically operated drive member. Alternatively or additionally, the axial displacement of the squeezing member may be induced by increasing or decreasing the pressure in one of first and second sub-cavities.

When actively moved driven, e.g. an external drive member, the squeezing member is configured to provide a peristaltic squeezing behavior. The squeezing member may be provided as a component of the container. It may be also provided separate from the container. It may be configured as a component of drive mechanism of a dispensing device, such as a peristaltic pump.

By moving a local deformation of at least one of first and second wall portions the hermetic separation between the first and second sub-cavities can be effectively displaced and moved in axial direction, thereby dynamically modifying the volume of first and second sub-cavities. In combination with the first and second outlets at opposite end sections of the casing the container may equally serve as a cavity for a liquid medicament to be dispensed as well as a sample container or waste container to receive a liquid. Such an embodiment may be of particular use for bed site systems. Axially displacing the squeezing element to decrease the volume of a first sub-cavity leads to a respective increase of the volume of the second sub-cavity. As a liquid substance, such like a medicament is dispensed from the first sub-cavity via the first outlet another liquid substance can be drawn into the second sub-cavity via the second outlet, which is then actually behaving as an inlet.

In another embodiment the at least one of the outlets comprises a check valve. A check valve provides a unidirectional flow of the liquid substance out of the cavity. Use of at least one or several check valves is of particular benefit with multiple chamber containers. By means of one or several check valves a cross-contamination of a liquid medicament in the first sub-cavity by a medicament originally located in the second sub-cavity can be effectively prevented and vice versa. By means of at least one or several check valves a mixing of multiple liquid medicaments will exclusively occur downstream of a check valve but not inside a sub-cavity. Typically, the at least one or several check valves are located upstream of a junction interconnecting first and second outlets of first and second sub-cavities, respectively.

In another aspect a drug delivery device for administering a liquid medicament is provided. The drug delivery device comprises a housing to accommodate a container as described above. The drug delivery device further comprises a drive mechanism which is configured to exert a dispensing pressure onto the casing of the container. Alternatively or additionally, the drive mechanism is operable to introduce a displacement fluid into the cavity of the container. Introduction of a displacement fluid may also increase the inside pressure of the cavity thus leading to a well-defined dispensing of the liquid medicament from the cavity. It is of particular benefit to make use of a displacement fluid that is insoluble with regards to the liquid medicament. The displacement fluid, which may be also denoted as a driving fluid, may be a liquid or a gaseous substance. It should be physiologically inert for not affecting the patient.

Depending on the specific configuration of the container the at least first outlet may be operable to dispense the liquid medicament from the cavity as well as to receive the displacement fluid from outside and to urge the displacement fluid into the cavity. It is also conceivable, that first and second outlets located at opposite end sections of the casing selectively provide ingress of a displacement fluid into the cavity and dispensing of the liquid medicament from the cavity, respectively. It is hence conceivable, that the first outlet is exclusively configured to provide dispensing of a medicament and that a second outlet is exclusively configured to provide ingress of the displacement fluid into the cavity. Both outlets may be provided with a respective check valve in order to prevent a flow of the medicament or of the displacement fluid in a wrong or undesired direction.

In another embodiment the container is actually arranged inside the housing of the drug delivery device. It is operably engageable with the drive mechanism of the drug delivery device. It may be operably and hence mechanically engaged with the drive mechanism. The container is readily filled with the liquid medicament.

The drug delivery device may be configured as a disposable drug delivery device which is intended to be discarded in its entirety once the liquid medicament inside the container has been used up or when the container is empty. Alternatively the drug delivery device may be configured as a re-usable drug delivery device, wherein the container is replaceable by a new one when empty. The drug delivery device and the drive mechanism are hence usable for a series and multiple exchangeable medicament containing containers as described above. The drug delivery device may be configured as an injection device, such as an injection pen. The drug delivery device may also be designed and configured as an infusion pump, as a peristaltic pump or as a so-called auto-injector. The drug delivery device may be further equipped with a drive mechanism having at least one squeezing member to apply a pressure onto the flexible casing.

With a casing of elongated shaped extending in a longitudinal axial direction and with at least one outlet at one longitudinal end the squeezing member of the drug delivery device may be configured to compress the casing's sidewall(s) in a direction perpendicular to the axial direction thereby forming increasing an inside pressure to expel a well-defined amount of the liquid substance from the container. In some embodiments the pressure member may be displaceable relative to the casing along the casing's longitudinal axial direction so as to move a locally compressed sidewall section of the casing in axial direction. In this way first and second sub-cavities formed by the compressed sidewall section that are brought in mutual contact with their inside sections can be enlarged and diminished. For instance, a size of the second sub-cavity at can be increased at the expense of the size of the first sub-cavity or vice versa.

The container is not limited to injection devices. It is also universally applicable for other types of drug delivery devices, such as inhalers. In one embodiment the drug delivery device comprises comprise an inhaler of the drug delivery device is configured as an inhaler.

In some embodiments, the casing comprises at least one of an elastomeric material, a flexible thermoplastic material, a layer of polymeric material or combinations, composites and laminates thereof.

Furthermore and according to further embodiments, the casing may comprise at least one of the following materials: thermoplastic elastomers (TPE), silicon rubber, butadiene rubber (BR), styrene butadiene rubber (SBR), styrene-ethylene/butylene-styrene type polymers (SEBS), LDPE, LLDPE, ethylene vinyl acetate (EVA), random copolymers of VP, polybutene-1, COC- or COP-based elastomers.

In particular when the casing comprises a comparatively thin layer of polymeric material, one of the following materials or combinations thereof can be used to form the casing: MDPE, high-density polyethylene (HDPE), PP, in form of homopolymer, random or heterophasic copolymers, polybutene-1, COC, COP, polymethylene pentane, PET, Polyethylenterephthalat Glycol (PET-G), PBT, PC, SAN or MABS. In general, the casing may comprise at least one or a combination of the above mentioned materials.

According to another embodiment, the casing comprises a multilayer structure. Hence, the casing comprises at least two substantially overlapping layers of different materials. Here, a combination of comparatively thin layers or foils of even rigid materials, such as MDPE, HDPE, PP, polybutene-1, COC, COP, polymethylene pentane, PET, PET-G, PBT, PC, PS, SAN, MABS and arbitrary combinations thereof can be used to form the casing. Especially when comprising a multilayer structure, the casing may also comprise at least one layer of polychlorotrifluoroethylene (PCTFE), polyamide (PA), ethylene-vinyl alcohol (EVOH) or polyparylene that can be used as barrier layer in a multilayer structure.

The barrier properties of said materials can be further improved by the use of passive barrier additives, such as polymer platelets of e.g. PA or EVOH, inorganic fillers, such as $SiO_2$, talc, and/or nanocomposites, such as nanoclays. Moreover, also active barrier additives, such as molecular sieves or chemical reactants, including oxidizable compounds may help to reduce the ingress of gaseous or liquid substances. Alternatively or in addition, coatings or laminates are generally applicable to improve the barrier properties of the casing.

The filaments can be made from any plastic material that is configured to form filaments. Typically, plastic materials such as polyamide or polyethylene may be used for the formation of the filaments.

The term "drug" or "medicament", as used herein, means a pharmaceutical formulation containing at least one pharmaceutically active compound,
wherein in one embodiment the pharmaceutically active compound has a molecular weight up to 1500 Da and/or is a peptide, a proteine, a polysaccharide, a vaccine, a DNA, a RNA, an enzyme, an antibody or a fragment thereof, a hormone or an oligonucleotide, or a mixture of the above-mentioned pharmaceutically active compound,
wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis,
wherein in a further embodiment the pharmaceutically active compound comprises at least one peptide for the treatment and/or prophylaxis of diabetes mellitus or complications associated with diabetes mellitus such as diabetic retinopathy,
wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser- Ser-Gly-Ala-Pro-Pro-Pro-Ser-NH2.

Exendin-4 derivatives are for example selected from the following list of compounds:
H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group -Lys6-NH2 may be bound to the C-terminus of the Exendin-4 derivative;
or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4 (1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4 (1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(02)25] Exendin-4 (1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2, H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(02)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2)25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp(O2)25, Asp28] Exendin-4(1-39)-(Lys)6-NH2;
or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while p and E have approximately 550 amino acids. Each heavy chain has two regions, the constant region ($C_H$) and the variable region ($V_H$). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H-H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

It will be further apparent to those skilled in the art that various modifications and variations can be made to the present disclosure without departing from the spirit and scope of the disclosure. Further, it is to be noted, that any reference numerals used in the appended claims are not to be construed as limiting the scope of the disclosure.

BRIEF DESCRIPTION OF THE DRAWINGS

In the following, various embodiments of the container and a drug delivery device are described in detail by making reference to the drawings, in which:

FIG. 15 shows one embodiment of a cross-section A-A according to FIG. 2, FIG. 16 shows a cross-section of another embodiment, FIG. 17 shows a cross-section A-A of a further embodiment of multiple filaments, FIG. 18 shows a longitudinal cross-section B-B according to FIG. 2 and FIG. 19 shows an alternative embodiment of the container in longitudinal cross-section according to B-B.

DETAILED DESCRIPTION

Figure 1:
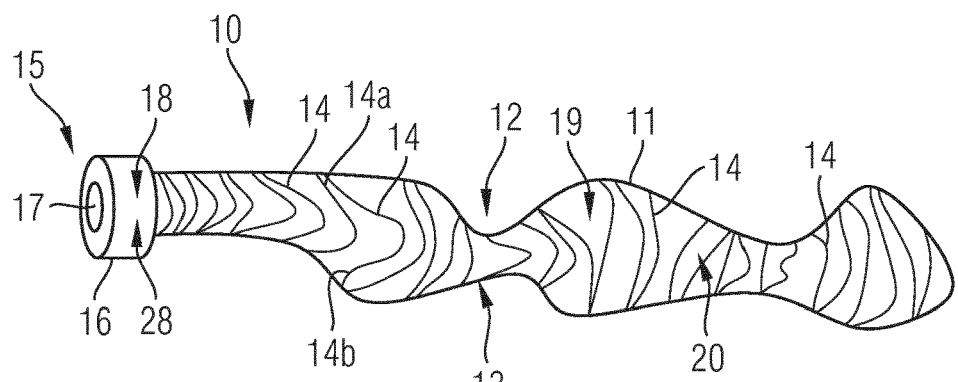
FIG. 1 schematically shows a first embodiment of the container in a non-inflated or non-filled configuration.

In FIG. 1 a container 10 for a liquid medicament 20 is schematically illustrated. The container 10 comprises a flexible casing 11 forming a substantially closed cavity 19. The cavity 19 is hence confined by the flexible casing 11. At one end, presently at a distal end section 4 the flexible casing 11 is connected to a first outlet 15. The outlet 15 may comprise a seal 17 that may be penetrated, e.g. by a double-tipped needle (not illustrated). The pierceable seal 17 may be fixed to the flexible casing 11 by means of a cap 16. The illustration of the outlet 15 is only exemplary and schematic. The outlet may be configured as a valve and may have a standardized connector, such as a male or female Luer-type connector. The outlet 15 may be further provided with a pressure regulator 18 or with a throttle valve 28 thereby enabling to keep the cavity 19 at a raised pressure level P larger than the environmental pressure outside the interior volume 19.

As it is further illustrated in FIG. 1, the casing 11 is flexible. It may comprise a plastic foil being substantially impenetrable or impervious to liquid and/or gaseous substances. As it is further illustrated in FIG. 1 the flexible casing 11 comprises a first wall portion 12, e.g. an upper wall portion and a second wall portion 13, e.g. a lower wall portion. There may be many different pairs of first and second wall portions 12, 13 provided that first and second wall portions 12, 13 are located opposite to each other. Hence, an inside surface 21 of the first wall portion 12 should face towards an inside surface 21 of the second wall portion 13.

Figure 2:
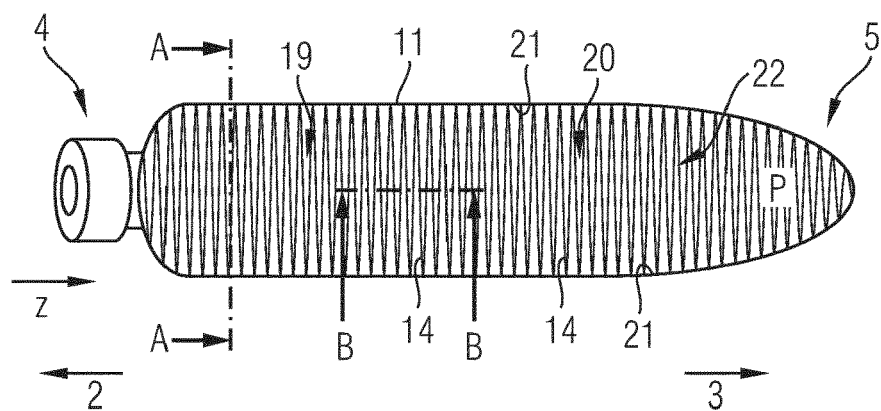
FIG. 2 shows the container according to FIG. 1 inflated to a maximum volume.

Between first and second wall portions 12, 13 there are provided multiple filaments 14. Each filament 14 has a first end 14a connected to the first wall portion 12 and further comprises an oppositely located second end 14b connected to the second wall portion 13. The multiplicity of filaments 14 provides structural and geometric stability to the casing 11 and hence to the entire container 10 once the cavity 19 is inflated to a maximum volume 22 as illustrated in FIG. 2. Due to a complete filling and hence inflating of the flexible cavity 19 oppositely located wall portions 12, 13 tend to separate from each other thereby tensioning and straining the multiplicity of filaments 14. The tensed and therefore straight-lined filaments 14 provide structural stability to the container 10. As soon as the container 10 is inflated to a predefined inside pressure P it is structurally self-supported and does not require any further housing or encapsulation for a pressure-based dispensing and withdrawal of the liquid medicament 20 from the cavity 19.

The length of individual filaments 14 defines the overall geometric structure of the flexible casing 11. As shown in FIG. 2, the container 10 comprises an elongated shape. It extends in an axial direction (z). As it is further apparent from FIGS. 15-17 it may comprise either an oval or elliptic cross-section or even a radial symmetric and hence circular cross-section in a plane perpendicular to the axial direction (z). There may be provided tens or hundreds of individual filaments 14 extending between oppositely located wall portions 12, 13 of the flexible casing 11. The filaments 14 may be bonded or integrally formed with at least one of the first and second wall portions. The filaments 14 are non-stretchable and are hence tension-stable. Once the cavity 19 is inflated to a maximum volume 22 at which the filaments 14 are tensed and become straight-lined a further expansion of the cavity and increase of its inner volume is effectively prevented by the tension-stable filaments 14.

There are conceivable various different configurations of filaments 14. Different configurations of filaments 14, 114, 214 are shown in FIGS. 15, 16 and 17. In the embodiment according to FIG. 15 the casing 11 comprises a somewhat oval-shaped cross-section in the imaginary plane 24 extending perpendicular to the axial direction (z). An upper sidewall section of the casing 11 forms the first wall portion 12 that is interconnected to a correspondingly-shaped lower sidewall section, hence to the second wall portion 13 by a multitude of filaments 14. As shown in FIG. 15 the filaments 14 extend substantially parallel with respect to each other. A first end 14a of each one of the filaments 14 is connected to the inside 21 of the first wall portion 14 and an opposite end, hence the second end 14b of all filaments 14 is connected to an inside 21 of the second wall portion 13.

The embodiment as shown in FIG. 16 is rather similar to the embodiment as shown in FIG. 15 with the exception that adjacently arranged or neighboring filaments 114 extend at alternating angles thereby forming a zigzag structure in the imaginary plane 24. Here, every second, hence the first, the third, the fifth, the seventh filament extends substantially parallel with respect to each other whereas the filaments therebetween, hence the second, the fourth, the sixth, the eighth filaments also extend substantially parallel to each other but at a certain angle with regard to the first, third and fifth filaments 114 therebetween.

Another configuration is shown in FIG. 17. There, the flexible casing 11 is substantially circular symmetric. Here, various filaments extend through the radial center of the cavity 19, wherein the center substantially coincides with the longitudinal symmetry axis of the container 10. With the embodiment as shown in FIG. 17 it is of particular benefit, when the multiple filaments 14 do not intersect in the radial center of the cross-section of the casing 11 but when the various filaments 214 are axially separated from each other. Here, each one of the filaments 214 extends parallel to the imaginary plane or even lies in the imaginary plane but filaments separated in axial direction, hence perpendicular to the cross-section according to FIG. 17 are positioned and located at a predefined axial offset.

With any of these configurations as shown in FIGS. 15-17 the geometric structure of the flexible casing 11 can be enhanced and stabilized as soon as the cavity 19 is inflated to a predefined inside pressure.

In FIG. 18 a cross-section along B-B according to FIG. 2 is given. Here, the various and parallel extending filaments 14 are arranged and fixed to the first wall portion 12 and to the second wall portion 13 in accordance with a rectangular or quadratic pattern. By means of such a regular and homogeneous spatial distribution of multiple filaments 14 a structurally stable container 10 can be provided. Another configuration of filaments is shown in FIG. 19. There, the filaments 114 are arranged in accordance to a hexagonal pattern. In other words, the filaments are located at the corners or edges of regular-shaped triangles thereby forming a hexagonal pattern of filaments 114 in a plane that coincides with the longitudinal or axial direction (z).

Figure 3:
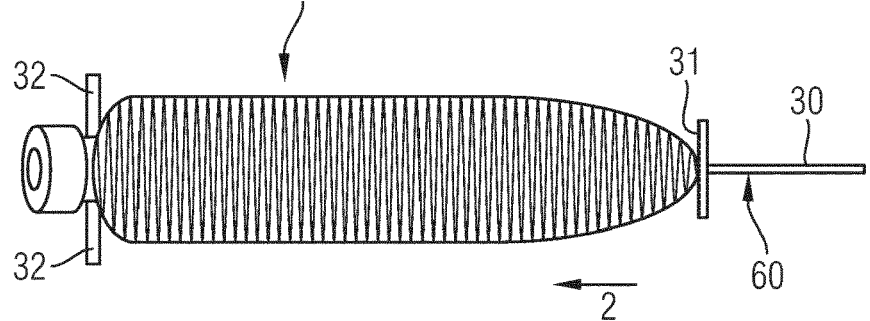
FIG. 3 shows the interaction of the container of FIG. 2 with the drive mechanism of a drug delivery device.
Figure 4:
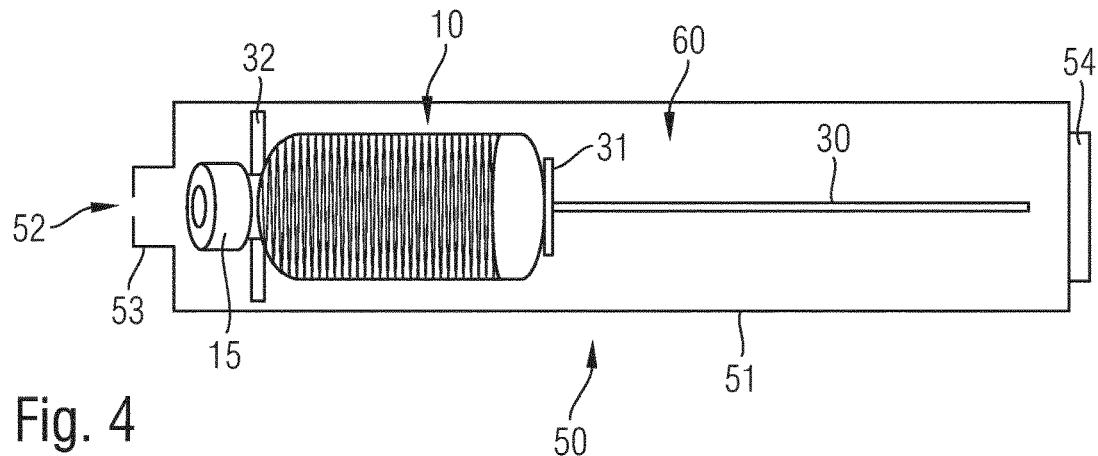
FIG. 4 shows the container inside a drug delivery device during or after dispensing of an amount of the liquid medicament, FIG. 5 schematically shows another implementation of a drive mechanism in an initial configuration.

In FIGS. 3 and 4 the interaction with the container 10 with a drug delivery device 50 is schematically illustrated. For dispensing of a well-defined amount of the liquid medicament 20 from the cavity 19 the container 10 is assembled inside a housing 51 of a drug delivery device 50 as shown in FIG. 4. A distal end section 4 facing in distal direction 2 of the container 10 is brought at least in mechanical contact with an abutment 32 provided at the interior of the drug delivery device 50. In this way the container 10 can be positionally fixed inside the drug delivery device 50. Instead of an abutment 32 it is also conceivable that the container 10 is fixed inside the drug delivery device 50 through its outlet 15.

At the opposite end, hence at the proximal end section 5 the container 10 is in operable engagement with a drive mechanism 60 of the drug delivery device 50. Typically, the drive mechanism 60 comprises a longitudinally or axially displaceable plunger 30 having a pressure piece 31 at its distal end section. As it is apparent from a comparison of FIGS. 3 and 4 the plunger 30 or the piston rod is displaceable in the distal direction 2 so as to squeeze, to compress and/or to deform the proximal end section 5 of the casing 11 thereby at least temporally increasing the inside pressure in the cavity.

When the inside pressure is raised above a predefined initial pressure value the outlet 15, in particular the pressure regulator 18 and/or the throttle valve 28 of the outlet 15 supports and allows escapement of a well-defined amount of the liquid medicament 20 until the pressure inside the cavity 19 approaches the previous initial pressure value. Due to the application of a distally directed pressure through the plunger 30 a portion of the casing 11 is subject to a local deformation. However, the cavity 19 remains pressurized and so the residual cavity 19 remains structurally stable due to the stabilizing effect and impact of the filaments 14.

As it is further illustrated in FIG. 4, the housing 51 of the drug delivery device 50 may comprise a socket 53 near a distal end section. The socket 53 may define an outlet 52 through which the liquid medicament 20 may be dispensed. The socket 53 may be configured to releasably engage with a correspondingly-shaped hub or socket of a piercing assembly, such as a disposable and double-tipped injection needle. It is also conceivable that the socket 53 comprises a standardized connection structure, such as a male or female Luer-connector by way of which a tube system may be connectable to the outlet 15 of the container 10 in a fluid transferring way. The drug delivery device 50 may further comprise at least one dose member 54 by way of which setting and/or dispensing of a dose of the medicament of a variable or fixed size may be individually controlled by a user of the device.

Figure 5:
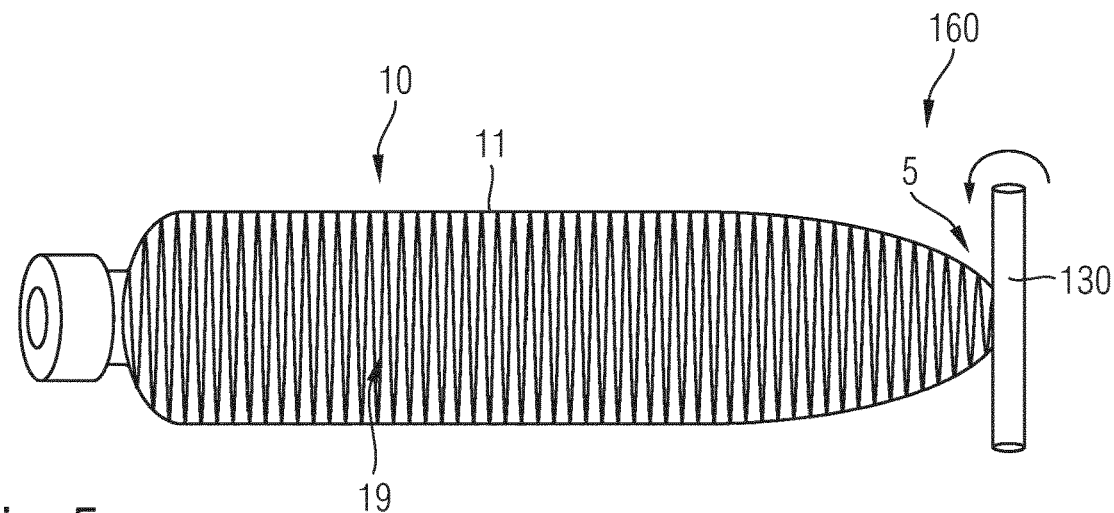
Figure 6:
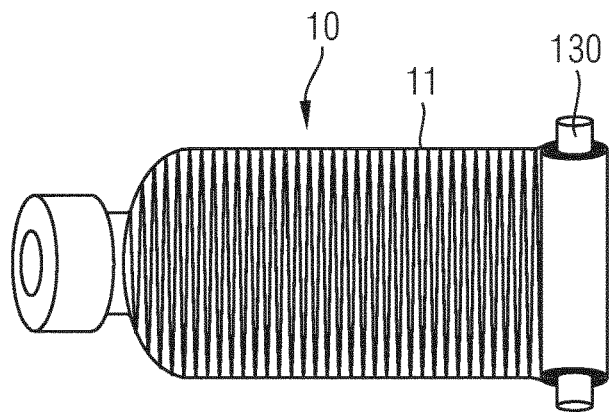
FIG. 6 shows the configuration according to FIG. 5 after dispensing of an amount of the medicament.
Figure 7:
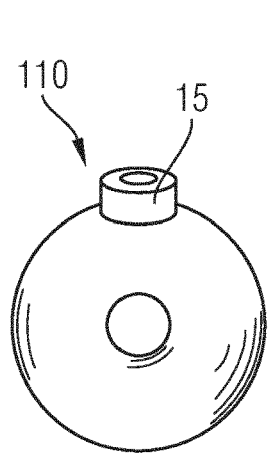
FIG. 7 shows another embodiment of the container.

In FIGS. 5 and 6 a different drive mechanism 160 is exemplary illustrated. Here, the proximal end section 5 of the casing 11 is rollable or coilable by means of a tubular-shaped coiling member 130. Here, the coiling member 130 is connectable to an outside facing portion of the proximal end section 5 of the flexible casing 11 by rotating the coiling member 130 the proximal end section 5 of the casing 11 will be coiled up onto the rotating coiling member 130. This leads to a continuous collapsing of first and second wall portions 12, 13 of the casing 11, thereby constantly decreasing the volume of the cavity 19 so that the inside pressure P raises and leads to a well-defined expelling of the liquid medicament 20 from the cavity 19. A partially coiled up configuration is finally shown in FIG. 6.

Figure 8:
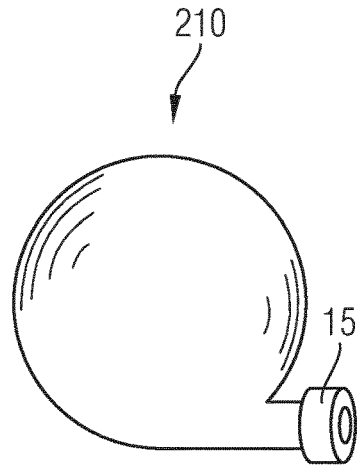
FIG. 8 shows another embodiment of the container.
Figure 9:
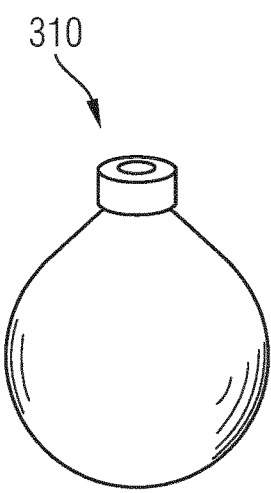
FIG. 9 shows a further embodiment of the container.
Figure 10:
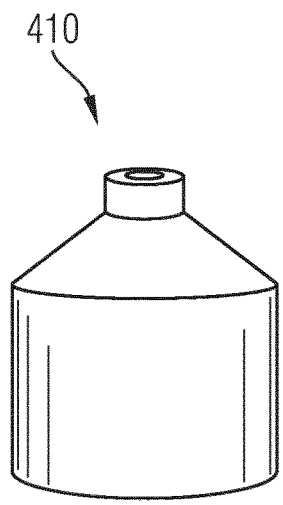
FIG. 10 shows another embodiment of the container.

In FIGS. 7, 8, 9 and 10 various different geometric configurations of containers for the liquid medicament are illustrated. The container 110 according to FIG. 7 comprises a toroidal or torus-like shape. The container 210 as shown in FIG. 8 is of disc shape or spherical shape. Here, the at least first outlet 15 extends in tangential direction from the outer circumference of the container 210. The container 310 as shown in FIG. 9 is bulb-shaped. The further container 410 according to FIG. 10 is of somewhat cylindrical shape. Various geometric shapes of the containers 10, 110, 210, 310, 410 can be easily designed and defined by the use of suitable filaments.

Figure 11:
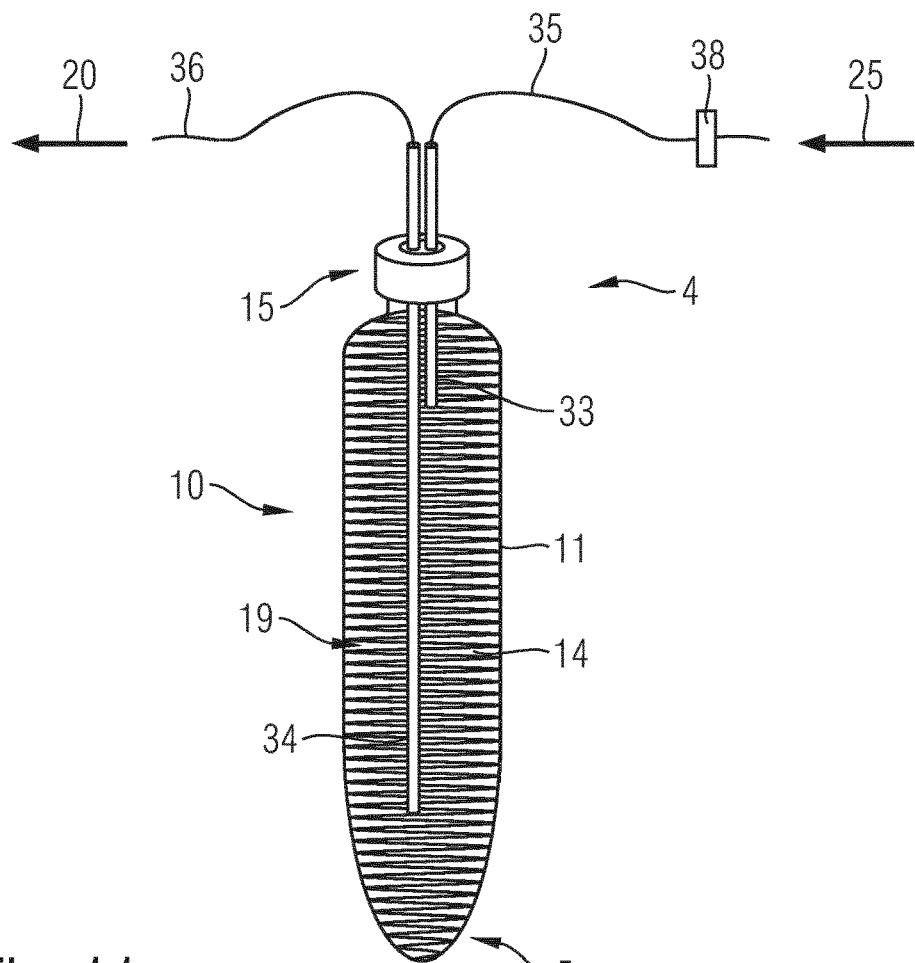
FIG. 11 shows a further embodiment of the container according to FIG. 2 configured for introduction of a displacement fluid into the cavity of the container.

In the embodiment according to FIG. 11 the container 10 as described in connection with FIGS. 1 and 2 is oriented in a vertical direction so that the outlet 15 forms an upper end thereof. Here, the outlet 15 is penetrated by two pipes, namely an inlet pipe 33 and an outlet pipe 34. The outlet pipe 34 is longer than the inlet pipe 33. Its lower end is located at or near a bottom, hence at the proximal end section 5 of the container 10. The shorter inlet pipe 33 terminates near a distal end 4 section, hence near the upper end of the cavity 19. The outlet pipe 34 is in fluid connection with an outlet tube 36 and the inlet pipe is connected with an inlet tube 35 outside the cavity 19.

Through the inlet pipe 33 a displacement fluid 25 is introducible into the cavity 19. In this way the inside pressure P can be raised to such a degree that medicament 20 located in the vicinity of the lower portion or lower end of the outlet pipe 34 is urged through the outlet pipe 34 and through the outlet tube 36. In the present embodiment it is of particular benefit when the displacement fluid 25 to be urged into the cavity 19 is insoluble with regard to the medicament 20. The displacement fluid 25 may be a gaseous or a liquid substance. In the vertically-oriented configuration of the container 10 as shown in FIG. 11 it is of particular benefit when the displacement fluid 25 and the medicament 20 have different specific weights. With the illustrated embodiment the displacement fluid 25 is of lower density than the liquid medicament 20.

Figure 12:
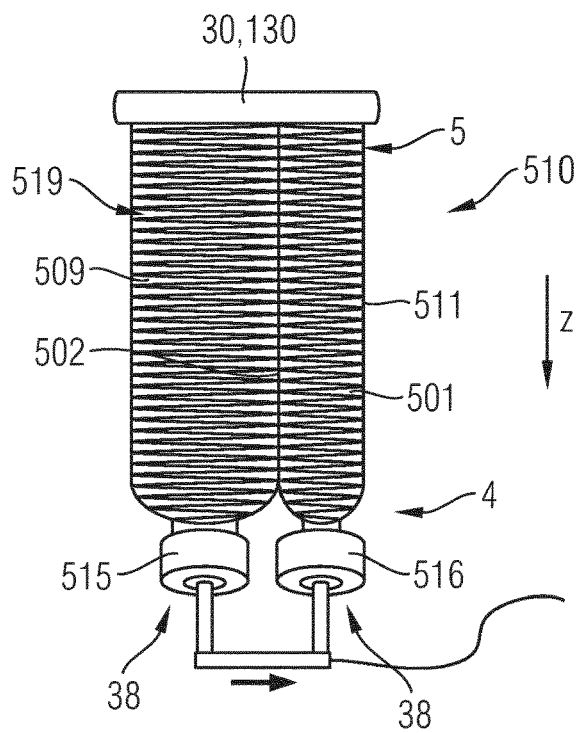
FIG. 12 shows a first embodiment of a multi-chamber container.
Figure 13:
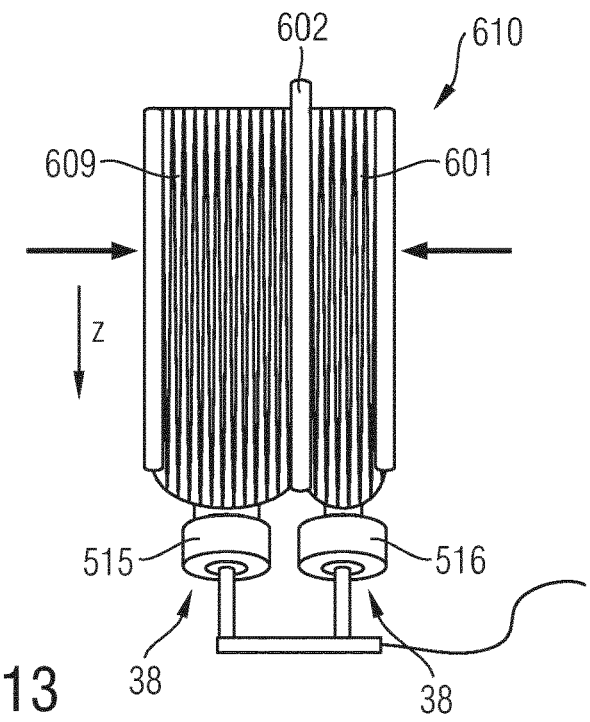
FIG. 13 shows another embodiment of a multi-chamber container.
Figure 14:
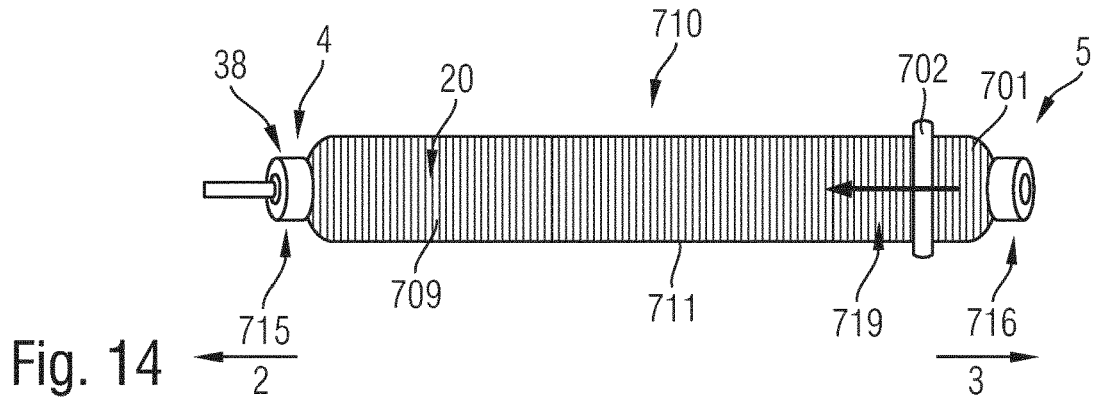
FIG. 14 shows a further embodiment of a container.

In FIGS. 12-14 various further embodiments are illustrated in which the container 510, 610, 710 comprises a multi-chamber structure. In the embodiment of FIG. 12 the container 510 comprises a flexible casing 511 that is divided into a first sub-cavity 509 and a second sub-cavity 501 by a separation wall 502 extending all along the cavity 519 from a proximal end section 5 to a distal end section 4 of the casing 511. The separation wall 502 is impenetrable and impervious for the liquid medicament 20. In this way different liquid medicaments can be stored and provided in the two separate sub-cavities 501, 509.

Similar as described above in connection with FIG. 3 or 5 the flexible casing 511 is either compressible or squeezable towards its distal end section 4 by means of a plunger 30 or by means of a coiling member 130. Since the first and the second sub-cavities 509, 501 extend both along the axial direction (z) both sub-cavities 501, 509 are equally subject to an increased inside pressure as soon as the drive mechanism 60, 160 of a drug delivery device 50 exerts distally directed pressure to the proximal end section 5 of the flexible casing 511.

In this way two different liquid medicaments 20 can be expelled from each one of the first and the second sub-cavities 509, 501. With multi-chamber embodiments of the container 510 it is of particular benefit when each sub-cavity 501, 509 not only comprises a separate first and second outlet 515, 516, respectively but when each one of first and second outlets 515, 516 is provided with a check valve 38 in order to prevent a backflow or reflux of the liquid medicament into any one of the sub-cavities 501, 509 and/or to prevent cross-contamination of liquid substances or liquid medicaments located in the first and second sub-cavities 501, 509, respectively.

The container 610 as shown in FIG. 13 is somewhat similar to the container 510 as shown in FIG. 12. But here the container 610 is configured for a compression in a direction perpendicular to the axial direction (z) of the container 610. Here, the separation wall 602 extends completely through the container 610 and even protrudes from the outer circumference of the container 610. The container 610 can be positionally fixed inside a housing 51 of a drug delivery device 50 by means of the separation wall 602. Consequently, the separation wall 602 may serve and act as a mechanical support and as a mount for fixing the container 610 inside the drug delivery device 50. It is then also possible to apply different pressures to the first sub-cavity and the second sub-cavity 609, 601 of the multi-chamber container 610. Accordingly, the medicaments located in different sub-cavities 609, 601 can be dispensed sequentially or at different mixing ratios.

The separation wall 602 may be also formed by two overlapping sidewalls of laterally adjacently arranged containers. A container 610 as shown in FIG. 13 may be formed or constituted by two individual containers, each of which having a flexible casing and an own cavity 601, 609. Then, the separation wall 602 would be formed by two sidewalls of the two individual containers that are connected to each other, e.g. by means of an adhesive or by means of welding.

The further embodiment of the container 710 as shown in FIG. 14 comprises a flexible casing 711 that extends in a longitudinal direction, hence along an axial distal direction 2 and an axial proximal direction 3. Here, oppositely located distal and proximal end sections 4, 5 of the container 710 are each provided with a separate outlet 715, 716. A first outlet 715 is in fluid communication or fluid connection with a first sub-cavity 709 and the oppositely arranged second outlet 716 is in fluid communication or fluid connection with the second sub-cavity 701.

There is further illustrated a squeezing member 702 by way of which first and second wall portions of the casing 711 can be squeezed in lateral or transverse direction, i.e. perpendicular to the axial direction 2, 3. The first and second walls, or a single, e.g. cylindrical- or oval-shaped sidewall of the casing 711 is compressible inwardly to such an extent that first and second oppositely located wall portions collapse to such an extent that their inside facing sections mutually connect. The pressure applied to the first and second walls can be as high so that the interconnected walls form a kind of a hermetic seal effectively dividing the cavity 719 of the elongated casing 711 into a first sub-cavity 709 and a second sub-cavity 701. The sub-cavities 701, 709 may be subject to size modifications, simply by moving the squeezing member 702 along the axial direction 2, 3. When moving the squeezing member 702 in distal direction 2, the second sub-cavity 701 is increased at the expense of the first sub-cavity 709. Then, a liquid substance can be dispensed from the first sub-cavity 709 while another liquid substance can be drawn into the first sub-cavity 701 or vice versa, namely when the squeezing member 702 is moved in proximal direction 3.

In this way, the volume or the size of the second sub-cavity 701 can be increased at the expense of the size of the first sub-cavity 709. Here, the first sub-cavity 709 may be configured to accommodate and to dispense a liquid medicament 20 whereas the further sub-cavity 701 can be used for sample collection. Consequently, the first outlet 715 may be provided with a check valve 38 only allowing dispensing of the liquid medicament 20 from the sub-cavity 709 whereas the oppositely located second outlet 716 actually serves as an inlet. The inlet 716 may be also provided with a check valve 38 that exclusively provides ingress of a liquid substance into the second sub-cavity 701.

Such a multi-chamber embodiment with simultaneously increasing and decreasing volumes of first and second sub-cavities 709, 701 is of particular benefit for bed site systems. Here, the medicament container fulfills a double function. It does not only provide and store a liquid medicament but simultaneously acts and provides a sample container to collect sample fluids or waste products.

The squeezing member 702 may belong to a drive mechanism of a drug delivery device. It may roll along the outside of the sidewall of the casing 711 in axial direction 2, 3 while keeping the pressure applied inwardly to the sidewall at a rather constant level. As shown in FIG. 14 the filaments may extend in longitudinal or axial direction. Alternatively, the filaments may be arranged along the transverse direction or laterally, i.e. substantially perpendicular to the axial direction 2, 3. With an elongated and tubular shaped casing 711 the filaments may extend along a radial direction. With transversely or radially extending filaments at least in those axial sections of the casing 711 that are located remote or offset from the momentary position of the squeezing member 702 can be kept dimensionally stable.

REFERENCE NUMBERS 2 distal direction
3 proximal direction
4 distal end section
5 proximal end section 10 container
11 casing
12 wall portion
1313 wall portion
14 filament
14a first end
14b second end
15 outlet
16 cap
17 seal
18 pressure regulator
19 cavity
20 medicament
21 inside
22 maximum volume
24 imaginary plane
25 displacement fluid
28 throttle valve
30 plunger
31 pressure piece
32 abutment
33 inlet pipe
34 outlet pipe
35 inlet tube
36 outlet tube
38 check valve
50 drug delivery device
51 housing
52 outlet
53 socket
54 dose member
60 drive member
110 container
114 filament
130 coil member
160 drive mechanism
210 container
214 filament
310 container
410 container
501 sub-cavity
502 separation wall
509 sub-cavity
510 container
511 casing
515 outlet
516 outlet
519 cavity
601 sub-assembly
602 separation wall
609 sub-cavity
610 container
701 sub-cavity
702 squeezing member
709 sub-cavity
710 container
711 casing
715 outlet
716 outlet
719 cavity

The invention claimed is:

1. A container for a liquid medicament, the container comprising:
at least one flexible casing forming at least one cavity configured to receive the medicament, wherein the casing comprises a first wall portion and a second wall portion, wherein the second wall portion is located opposite to the first wall portion;
at least a first outlet in fluid connection with the cavity and extending through the casing; and
multiple filaments extending through the cavity, wherein each of the multiple filaments comprises a first longitudinal end and a second longitudinal end, wherein the second longitudinal end is opposite to the first longitudinal end, and wherein each of the first longitudinal ends of the filaments are connected to the first wall portion and each of the second longitudinal ends of the filaments are connected to the second wall portion.

2. The container according to claim 1, wherein the filaments are tension-stable.

3. The container according to claim 1, wherein the cavity is inflatable to a maximum volume and to a predefined inside pressure at least until the filaments are tensed and straightlined.

4. The container according to claim 3, wherein each of the casing, the first wall portion, the second wall portion, and the cavity are non-expandable or non-stretchable beyond the maximum volume.

5. The container according to claim 1, wherein the first outlet comprises at least one of a pressure regulator or a throttle valve.

6. The container according to claim 1, wherein the casing is of elongated shape and extends in an axial direction, and wherein the casing comprises a distal end section and a proximal end section separated along the axial direction.

7. The container according to claim 6, wherein the first outlet is located at the distal end section and wherein the proximal end section is deformable, squeezable, or compressible towards the distal end section.

8. The container according to claim 6, wherein the proximal end section of the casing is coilable towards the distal end section.

9. The container according to claim 6, wherein at least some of the filaments are located in a virtual plane extending substantially perpendicular to the axial direction of the casing.

10. The container according to claim 1, wherein at least some of the filaments extend substantially parallel to each other, wherein at least some of the filaments form a zigzag structure and wherein at least some of the filaments extend radially with regard to the axial direction, wherein the axial direction coincides with a symmetry axis of the container.

11. The container according to claim 1, wherein at least some of the filaments extend substantially parallel to each other, wherein at least some of the filaments form a zigzag structure or wherein at least some of the filaments extend radially with regard to the axial direction, wherein the axial direction coincides with a symmetry axis of the container.

12. The container according to claim 1, further comprising:
a separation wall configured to divide the cavity into a first sub-cavity and a second sub-cavity; and
a second outlet,
wherein the first outlet is in fluid connection with the first sub-cavity and the second outlet is in fluid connection with the second sub-cavity.

13. The container according to claim 12, wherein at least one of the first outlet or the second outlet comprises a check-valve.

14. The container according to claim 1,
wherein the first outlet and a second outlet are located at opposite end sections of the casing,
wherein the casing is elongated along an axial direction, wherein the casing is configured to become compressed by a squeezing member in a direction perpendicular to the axial direction to form a first sub-cavity and a second sub-cavity, and wherein the squeezing member is configured to be displaced along the axial direction to increase a size of the second sub-cavity at the expense of a size of the first sub-cavity or vice versa.

15. A drug delivery device for administering a liquid medicament, comprising:

a housing configured to accommodate a container, the container comprising:

at least one flexible casing forming at least one cavity configured to receive the medicament, wherein the casing comprises a first wall portion and a second wall portion, wherein the second wall portion is located opposite to the first wall portion;

at least a first outlet in fluid connection with the cavity and extending through the casing; and multiple filaments extending through the cavity, wherein each of the multiple filaments comprises a first longitudinal end and a second longitudinal end, wherein the second longitudinal end is opposite to the first longitudinal end, and wherein each of the first longitudinal ends of the filaments are connected to the first wall portion and each of the second longitudinal ends of the filaments are connected to the second wall portion, a drive mechanism configured to exert a dispensing pressure onto the casing of the container, or to introduce a displacement fluid into the cavity of the container.

16. The drug delivery device according to claim 15, wherein the container is arranged inside the housing, and wherein the container is filled with the liquid medicament.

17. A container for a liquid medicament, the container comprising:

at least one flexible casing forming at least one cavity configured to receive the medicament, wherein the casing comprises a first wall portion and a second wall portion, wherein the second wall portion is located opposite to the first wall portion;

at least a first outlet in fluid connection with the cavity and extending through the casing; and multiple filaments extending through the cavity, wherein each of the multiple filaments comprises a first end and a second end, wherein the second end is opposite to the first end, and wherein each of the first ends of the filaments are connected to the first wall portion and each of the second ends of the filaments are connected to the second wall portion, wherein the cavity is inflatable to a maximum volume and to a predefined inside pressure at least until the filaments are tensed and straight-lined.

18. The container according to claim 17, wherein each of the casing, the first wall portion, the second wall portion, and the cavity are non-expandable or non-stretchable beyond the maximum volume.

* * * * *